(12) United States Patent
Blazej et al.

(10) Patent No.: US 8,557,742 B2
(45) Date of Patent: Oct. 15, 2013

(54) METHOD OF ENHANCING ENZYME ACTIVITY

(75) Inventors: Robert G. Blazej, San Francisco, CA (US); Brian M. Paegel, Jupiter, FL (US)

(73) Assignees: Novozymes A/S, Bagsvaerd (DK); The Scripps Research Institute, La Jolla, CA (US)

( * ) Notice: Subject to any disclaimer, the term of this patent is extended or adjusted under 35 U.S.C. 154(b) by 185 days.

(21) Appl. No.: 12/935,249

(22) PCT Filed: Apr. 3, 2009

(86) PCT No.: PCT/US2009/039558
§ 371 (c)(1),
(2), (4) Date: Nov. 1, 2010

(87) PCT Pub. No.: WO2009/124296
PCT Pub. Date: Oct. 8, 2009

(65) Prior Publication Data
US 2011/0046012 A1    Feb. 24, 2011

Related U.S. Application Data

(60) Provisional application No. 61/042,637, filed on Apr. 4, 2008.

(51) Int. Cl.
*C40B 30/08*    (2006.01)
(52) U.S. Cl.
USPC .................................................. 506/7; 506/11
(58) Field of Classification Search
USPC ............................................................. 506/7
See application file for complete search history.

(56) References Cited

U.S. PATENT DOCUMENTS

| 6,489,103 | B1 | 12/2002 | Griffiths et al. |
| 2007/0077572 | A1 | 4/2007 | Tawfik et al. |
| 2008/0076152 | A1 | 3/2008 | St-pierre et al. |

FOREIGN PATENT DOCUMENTS

| WO | WO 99/02671 | 1/1999 |
| WO | WO 2009/124296 | 10/2009 |

OTHER PUBLICATIONS

Levy et al. ("Direct selection of trans-acting ligase ribozymes by in vitro compartmentalization", RNS, 2005, vol. 11, pp. 1555-1562).*
Griffiths and Tawfik, ("Directed evolution of an extremely fast phosphotriesterase by in vitro compartmentalization", EMBO Journal, 2003, vol. 22, No. 1, pp. 24-35).*
Ghadessy et al. ("Directed evolution of polymerase function by compartmentalized self-replication", PNAS, 2001, vol. 98, No. 8, pp. 4552-4557).*

(Continued)

*Primary Examiner* — Ardin Marschel
*Assistant Examiner* — Richard L Manteuffel
(74) *Attorney, Agent, or Firm* — Emily M. Haliday; Weaver Austin Villeneuve & Sampson LLP

(57) ABSTRACT

Described are methods and means for enhancing enzyme activity toward insoluble substrates. This is achieved by means of in vitro compartmentalization in which an insoluble microparticle functions both as the enzyme substrate and as a structure for negative selection. Enhanced enzymes expressed from a microparticle-linked polynucleotide library preferentially degrade the microparticle releasing specific gene variants into solution. Gene variants encoding less active enzyme variants remain linked to the microparticle and may be removed through centrifugation, thus enriching the polynucleotide library for more active enzyme variants. These methods may be used to enhance cellulase and ligninase activity toward insoluble cellulosic biomass.

17 Claims, 4 Drawing Sheets

(56) References Cited

OTHER PUBLICATIONS

Zhang et al. ("Outlook for cellulose improvement: screen an selection strategies", Biotechnologies Advances, 2006, vol. 24, pp. 452-481).*
Levi et al., (RNA, 2005, vol. 11, pp. 1555-1562).*
International Search Report and Written Opinion dated Aug. 19, 2009 issued in PCT/US2009/039558 (WO 2009/124296).
International Preliminary Report on Patentability dated Oct. 5, 2010 issued in PCT/US2009/039558 (WO 2009/124296).
EP Extended Search Report and Written Opinion dated Mar. 2, 2012 issued in EP09727374.2 (P001EP).
Agresti et al. (2005) "Selection of ribozymes that catalyse multiple-turnover Diels-Alder cycloadditions by using in vitro compartmentalization." *Proc. Natl. Acad. Sci. U. S. A.* 102(45): 16170-16175.
Aharoni et al. (2005) "High-throughput screening of enzyme libraries: Thiolactonases evolved by fluorescence-activated sorting of single cells in emulsion compartments." *Chem. Biol.* 12(12): 1281-1289.
Freeman et al. (2004) "Screening of Large Protein Libraries by the Cell Immobilized on Adsorbed Bead' Approach" *Biotechnology and Bioengineering* 86(2): 196-200.
Griffiths et al. (2000) "Man-made enzymes: From design to in vitro compartmentalisation" *Current Opinion in Biotechnology* 11(4): 338-353.
Griffiths et al. (2006) "Miniaturising the laboratory in emulsion droplets." *TRENDS in Biotech.* 24(9): 395-402.
Mastrobattista et al. (2005) "High-throughput screening of enzyme libraries: In vitro evolution of a beta-galactosidase by fluorescence-activated sorting of double emulsions." *Chem. Biol.* 12(12): 1291-1300.
Schaerli et al. (2009) "The potential of microfluidic water-in-oil droplets in experimental biology" *Molecular Biosystems* 5(12): 1392-1404.
Schulein (2000) "Protein engineering of cellulases." *Biochim. Biophys. Acta-Protein Struct. Molec. Enzym.* 1543(2): 239-252.
Tawfik et al. (1998) "Man-made cell-like compartments for molecular evolution." *Nat. Biotechnol.* 16(7): 652-656.

* cited by examiner

```
Sequence 1527 BP; 320 A; 526 C; 411 G; 270 T; 0 other;
ttgtcccaaa atggcgccct cagttacact gccgttgacc acggccatcc tggccattgc    60
ccggctcgtc gccgcccagc aaccgggtac cagcacccccc gaggtccatc ccaagttgac   120
aacctacaag tgtacaaagt ccggggggtg cgtggcccag acacctcgg tggtccttga    180
ctggaactac cgctggatgc acgacgcaaa ctacaactcg tgcaccgtca acggcggcgt    240
caacaccacg ctctgccctg acgaggcgac ctgtggcaag aactgcttca tcgagggcgt    300
cgactacgcc gcctcgggcg tcacgacctc gggcagcagc ctcaccatga accagtacat    360
gcccagcagc tctggcggct acagcagcgt ctctcctcgg ctgtatctcc tggactctga    420
cggtgagtac gtgatgctga agctcaacgg ccaggagctg agcttcgacg tcgacctctc    480
tgctctgccg tgtggagaga acggctcgct ctacctgtct cagatggacg agaacggggg    540
cgccaaccag tataacacgg ccggtgccaa ctacgggagc ggctactgcg atgctcagtg    600
ccccgtccag acatggagga acggcacccct caacactagc caccagggct ctgctgcaa    660
cgagatggat atcctggagg gcaactcgag ggcgaatgcc ttgacccctc actcttgcac    720
ggccacggcc tgcgactctg ccggttgcgg cttcaacccc tatggcagcg gctacaaaag    780
gtgagcctga tgccactact acccctttcc tggcgctctc gcggttttcc atgctgacat    840
ggttttccag ctactacggc cccggagata ccgttgacac ctccaagacc ttcaccatca    900
tcacccagtt caacacggac aacggctcgc cctcgggcaa ccttgtgagc atcacccgca    960
agtaccagca aaacggcgtc gacatccccca gcgccagcc cggcggcgac accatctcgt   1020
cctgccgtc cgcctcagcc tacggcggcc tcgccaccat gggcaaggcc ctgagcagcg   1080
gcatggtgct cgtgttcagc atttggaacg acaacagcca gtacatgaac tggctcgaca   1140
gcggcaacgc cggcccctgc agcagcaccg agggcaaccc atccaacatc ctggccaaca   1200
accccaacac gcacgtcgtc ttctccaaca tccgctgggg agacattggg tctactacga   1260
actcgactgc gcccccgccc ccgcctgcgt ccagcacgac gttttcgact acacggagga   1320
gctcgacgac ttcgagcagc ccgagctgca cgcagactca ctgggggcag tgcggtggca   1380
ttgggtacag cgggtgcaag acgtgcacgt cgggcactac gtgccagtat agcaacgact   1440
gttcgtatcc ccatgcctga cgggagtgat tttgagatgc taaccgctaa aatacagact   1500
actcgcaatg cctttagagc gttgact   1527

(SEQ ID NO:1)
```

Fig. 3

```
Sequence 1340 BP;  244 A;  467 C;  328 G;  301 T;  0 other;
tttttttcttc agtcccactc agcaccagca acacagcgga catggccttc aagcagctct   60
tcgcagctat ctctctcgct ctcttgctct cggctgcgaa cgcggctgcg gtgatcgaga  120
agcgcgccac ctgttccaac ggcaagaccg tcggcgatgc gtcgtcgtgc gcttggttcg  180
acgtcctgga tgatatccag cagaacctgt ccacggcgg ccagtgcggc gctgaggcgc  240
acgagtcgat tcgtctcgtc ttccacgact ccatcgcaat tcgcccgcc atggaggcac  300
agggcaagtt cggcggcggt ggtgctgacg gctccatcat gatcttcgac gatatcgaga  360
ctgcgttcca ccctaacatc ggtctcgacg agatcgtcaa gctccagaag ccattcgttc  420
agaagcacgg tgtcaccct ggtgacttca tcgccttcgc tggtcgtgtc gcgctcagca  480
actgccctgg tgccccgcag atgaacttct tcactggtcg tgcacctgct acccagcccg  540
ctcctgatgg ccttgtcccc gagcccttcc acactgtcga ccaaatcatc aaccgtgtca  600
acgacgcagg cgagttcgat gagctcgagc ttgtctggat gctctccgcg cactccgtcg  660
cagcggtgaa cgacgtcgac ccgaccgtcc agggtctgcc ctttgactcg accccggaa  720
tcttcgactc ccagttcttc gtcgagactc agcttcgtgg taccgccttc cccggctctg  780
gtggcaacca aggcgaggtc gagtcgccgc tccctggcga aattcgcatc cagtccgacc  840
acactatcgc ccgcgactcg cgcacggcgt gtgaatggca gtccttcgtc aacaaccagt  900
ccaagctcgt cgatgacttc cagttcatct tcctcgccct cacccagctc ggccaggacc  960
cgaacgcgat gaccgactgc tcggatgtta tccgcagtc caagcccatc cctggcaacc 1020
tcccattctc gttcttcccc gctggcaaga ccatcaagga cgttgagcag gcgtgtgcgg 1080
agagcccctt ccgactctca ccactctccc gggccccgag acgtccgtcc agcgcatccc 1140
tccgcctccg ggtgcttaaa tgatgccata cagaatactc ctcaaaccga ctgtaacggt 1200
ggccggctaa ctcgtgacgg aacttcggct ttactagatt tcattcatcg tatctctgca 1260
cctaactacg aatctcattc gtctacttcc ttcttacgat attccttgcg cgtgggctta 1320
tgaaatatcg gtgcacatcc 1340

(SEQ ID NO:2)
```

*Fig. 4*

METHOD OF ENHANCING ENZYME ACTIVITY

CROSS-REFERENCE TO RELATED APPLICATIONS

This application is a 371 National Phase of PCT/US2009/039558, filed on Apr. 3, 2009, which claims priority to and benefit of USSN 61/042,637, filed on Apr. 4, 2008, which is incorporated herein by reference in its entirety for all purposes.

FIELD OF THE INVENTION

The present invention is in the technical field of protein engineering design and selection. More particularly, the present invention relates to enzyme enhancement by means of directed evolution.

BACKGROUND OF THE INVENTION

Cellulosic biomass is the most abundant renewable natural resource. Generated at a rate of ~100 billion dry tons/year by the biosphere, cellulosic biomass has the potential to replace the world's demand for diminishing fossil fuels. However, according to Zhang, Y. H. P. "One of the most important and difficult technological challenges is to overcome the recalcitrance of natural lignocellulosic materials, which must be enzymatically hydrolyzed to produce fermentable sugars." See, (Zhang, Y. H. P., et al., "Outlook for cellulase improvement: Screening and selection strategies." *Biotechnol. Adv.*, 2006, 24: 452-481).

Cellulose is a polysaccharide consisting of 100 to 20,000 β-1-4 linked glucose units. Cellulases, the class of enzymes that hydrolyze cellulose, have attracted immense interest for their ability to degrade cellulosic biomass into glucose for biofuel production. Three cellulase sub-classes (endoglucanase, exoglucanase, β-glucosidase) work synergistically to hydrolyze cellulose. Endoglucanases hydrolyze intramolecular β-1-4-glucosidic bonds in insoluble cellulosic material to produce new chain ends. Exoglucanases progressively hydrolyzed the chain ends liberating small water-soluble oligosaccharide products. The soluble products are finally hydrolyzed by β-glucosidase into glucose (Schulein, M., "Protein engineering of cellulases." *Biochim. Biophys. Acta-Protein Struct. Molec. Enzym.*, 2000, 1543(2): 239-252).

SUMMARY OF THE INVENTION

The invention includes a system for improving enzyme activity toward a solid substrate. In one aspect, the invention includes a method of selecting for enhanced cellulase activity by means of in vitro compartmentalization in which a cellulosic microparticle functions both as the targeted solid substrate and as a structure for negative selection. In another aspect, the microparticle may be composed of lignin or other insoluble substrate.

Various implementations of the invention include a system to generate a polynucleotide library. The library encodes enzyme variants having different activity toward the targeted solid substrate. The system further includes a means of linking individual or clonal copies of individual gene variants to a microparticle composed of the targeted solid substrate. The system also includes means for compartmentalizing individual microparticles with linked genes in an emulsion containing an in vitro transcription/translation reaction. Additionally, the system includes means for expressing each linked gene variant in order to produce enzyme in each emulsion compartment having different activity toward the microparticle. Microparticles within emulsion compartments containing highly active enzyme variants are degraded, thus liberating the linked gene variant from microparticle. Furthermore, the system includes means for breaking the emulsion compartments and selectively recovering the liberated gene variants that encode enzymes with enhanced enzyme activity toward the microparticle substrate. Further enzyme activity enhancement can be achieved by generating a new polynucleotide library derived from the recovered gene variants and repeating the steps above.

Other implementations of the invention may include the use of a cleavable linker between the gene variant and a non-reactive carrier microparticle. The linker may, for example, be composed of cellulose, hemicellulose, or lignin. Within emulsion compartments containing highly active enzyme variants, the linker is degraded, thus liberating the linked gene variant from the carrier microparticle.

The invention can include one or more of the following advantages. The invention utilizes a novel IVC-based, selection-mode approach to optimizing enzymatic activity of cellulases on insoluble cellulose substrates, and is extensible to optimizing enzymatic activity on any insoluble substrate. Enzyme selection is performed on natural insoluble cellulosic material. Therefore, enzyme activity is tailored to the actual substrate of commercial interest, not a surrogate soluble or fluorogenic substrate. Populations of $10^{10}$-$10^{12}$ gene variants can be surveyed, a vast improvement over screening-based approaches that are usually limited to 10,000 variants. Enzyme selection is performed completely in vitro, eliminating the organismal metabolic and genomic background that leads to off-target optimization.

These and other features and advantages of the present invention will be presented in more detail in the following specification of the invention and the accompanying figures, which illustrate, by way of example, the principles of the invention.

BRIEF DESCRIPTION OF THE DRAWINGS

The invention may be understood by reference to the following description taken in conjunction with the accompanying drawings that illustrate specific embodiments of the present invention.

FIG. 3 shows Sequence 1, which is the DNA sequence of the endoglucanase gene egl1 from *Trichoderma reesei* (EMBL Database #M15665).

FIG. 4 shows Sequence 2, which is the DNA sequence of the ligninase gene LiP H8 from *Phanerochaete chrysosporium* (EMBL Database #Y00262).

DETAILED DESCRIPTION

Definitions

Figure 1:
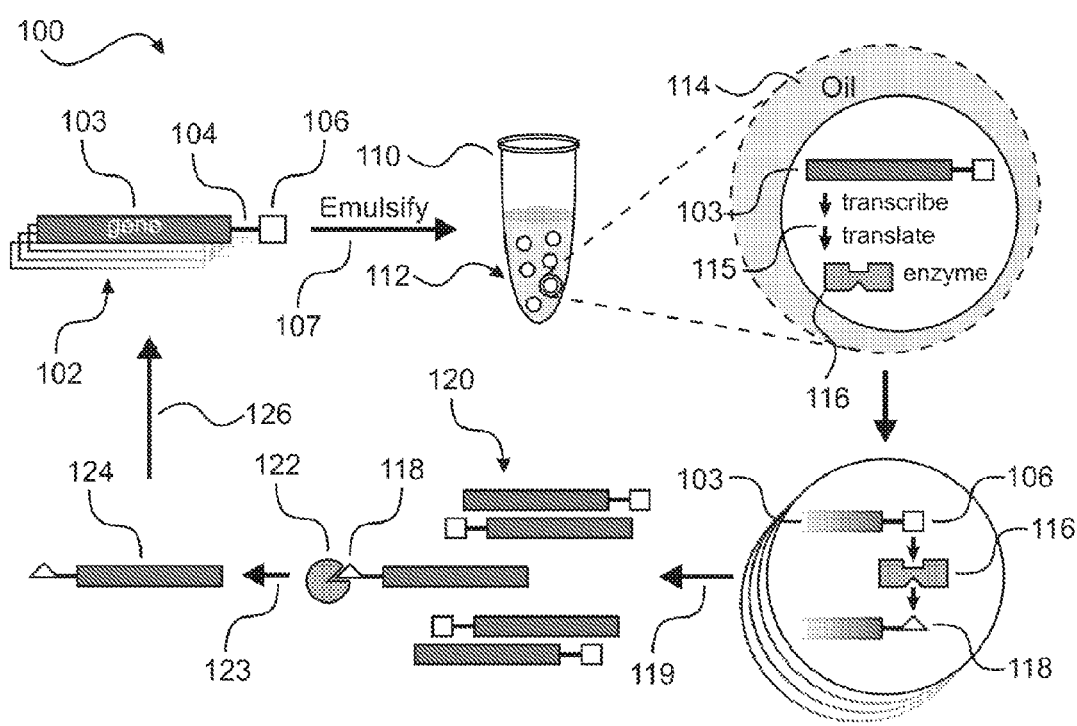
FIG. 1 is a diagrammatic representation of the process steps involved in directed evolution by means of in vitro compartmentalization (IVC).

Terms used in the claims and specification are defined as set forth below unless otherwise specified.

The term "polynucleotide" refers to a deoxyribonucleotide or ribonucleotide polymer, and unless otherwise limited, includes known analogs of natural nucleotides that can function in a similar manner to naturally occurring nucleotides.

The term "polynucleotide" refers to any form of DNA or RNA, including, for example, genomic DNA; complementary DNA (cDNA), which is a DNA representation of messenger RNA (mRNA), usually obtained by reverse transcription of mRNA or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

Polynucleotides are said to be "different" if they differ in structure, e.g., nucleotide sequence.

As used herein, the term "substrate" generally refers to a substrate for an enzyme; i.e., the material on which an enzyme acts to produce a reaction product.

An "insoluble substrate," as used herein, refers to an enzyme substrate that is not soluble in water at 37° C.

As used herein, a "solid phase" refers to any material that is a solid when employed in the selection methods of the invention. The solid phase is the material to which polynucleotides are linked to carry out these selection methods.

The term "linker," as used herein, refers to any moiety that attaches a polynucleotide to a solid phase.

The terms "amino acid" or "amino acid residue," include naturally occurring L-amino acids or residues, unless otherwise specifically indicated. The terms "amino acid" and "amino acid residue" also include D-amino acids as well as chemically modified amino acids, such as amino acid analogs, naturally occurring amino acids that are not usually incorporated into proteins, and chemically synthesized compounds having the characteristic properties of amino acids (collectively, "atypical" amino acids). For example, analogs or mimetics of phenylalanine or proline, which allow the same conformational restriction of the peptide compounds as natural Phe or Pro are included within the definition of "amino acid."

Protein Evolution Using In Vitro Compartmentalization

The present invention employs in vitro compartmentalization (IVC) for rapid and high throughput enzyme evolution. Instead of relying on a physical link between the genotype and phenotype as implemented in display technologies, IVC links genotype and phenotype by spatial confinement in a single aqueous droplet of a water-in-oil emulsion (Tawfik, D. S. et al., "Man-made cell-like compartments for molecular evolution." *Nat. Biotechnol.*, 1998, 16(7): 652-656; U.S. Pat. No. 6,489,103; WO 1999/002671 A1). IVC is presented diagrammatically in FIG. 1 (100). As practiced, an in vitro transcription/translation (IVTT) reaction is mixed with a solution containing the polynucleotide library (102). The polynucleotide library (102), commonly prepared by mutagenic amplification or recombination, contains gene variants (103) of the wild-type gene sequence linked by tether (104) to substrate moiety (106) (Cadwell, R. C. et al., "Mutagenic PCR." *PCR-Methods and Applications*, 1994, 3(6): S136-S140; Vartanian, J. P. et al., "Hypermutagenic PCR involving all four transitions and a sizeable proportion of transversions." *Nucleic Acids Res.*, 1996, 24(14): 2627-2631; Stemmer, W. P. C., "Rapid Evolution of a Protein in vitro by DNA Shuffling." *Nature*, 1994, 370(6488): 389-391; Zhao, H. M. et al., "Molecular evolution by staggered extension process (StEP) in vitro recombination." *Nat. Biotechnol.*, 1998, 16(3): 258-261). The polynucleotide library (102) and IVTT solution are mixed and dispersed (107) into a mineral oil/surfactant solution (114) to yield emulsion (110). The volume of an average droplet (112) in emulsion (110) determines the initial concentration of the polynucleotide library (102) solution such that on average only one gene variant (103) contained in polynucleotide library (102) will be present in any given aqueous droplet (112) in emulsion (110). Emulsion (110) is incubated at 30° C. whereupon the IVTT system transcribes and translates (115) gene variant (103) into protein enzyme variant (116) (Miller, O. J. et al., "Directed evolution by in vitro compartmentalization." *Nat. Methods*, 2006, 3(7): 561-570).

Once translated, protein variant (116) catalyzes the transformation of gene variant-linked substrate (106) into product (118) if protein variant (116) is catalytically active. Emulsion (110) is broken (119) via extraction or centrifugation, and gene variants (120) are recovered. In prior implementations of this technique, a positive selection (123) occurs, for example, when recovered gene variants (120) are passed though a column with binding affinity (122) for product (118). Gene variants (124) encoding catalytically superior protein enzyme variant and are retained. Gene variants (124) thus enriched are amplified via previously described mutagenic techniques to generate a refined polynucleotide library for further rounds of emulsification and selection.

Selection of desirable phenotypes using previously-practiced IVC methods was accomplished in a number of ways. The substrate was linked to the gene, and transformation of the gene-linked substrate tagged the successful genotype for affinity selection as described above (Agresti, J. J. et al., "Selection of ribozymes that catalyse multiple-turnover Diels-Alder cycloadditions by using in vitro compartmentalization." *Proc. Natl. Acad. Sci. U.S.A.*, 2005, 102(45): 16170-16175; Tawfik, D. S. et al., "Man-made cell-like compartments for molecular evolution." *Nat. Biotechnol.*, 1998, 16(7): 652-656). Alternatively, if the phenotype is polymerase activity, selection occurred via enrichment where more active polymerases amplify the gene co-encapsulated with the polymerase (Ghadessy, F. J. et al., "Directed evolution of polymerase function by compartmentalized self-replication." *Proc. Natl. Acad. Sci. U.S.A.*, 2001, 98(8): 4552-4557). High-throughput droplet screening via fluorescence activated cell sorting has also been used to identify and sequester genes encoding catalysts that transform a fluorogenic substrate or bind a fluorescent antibody specific for the target product (Griffiths, A. D. et al., "Directed evolution of an extremely fast phosphotriesterase by in vitro compartmentalization." *Embo J.*, 2003, 22(1): 24-35; Aharoni, A. et al., "High-throughput screening of enzyme libraries: Thiolactonases evolved by fluorescence-activated sorting of single cells in emulsion compartments." *Chem. Biol.*, 2005, 12(12): 1281-1289; Mastrobattista, E. et al., "High-throughput screening of enzyme libraries: In vitro evolution of a beta-galactosidase by fluorescence-activated sorting of double emulsions." *Chem. Biol.*, 2005, 12(12): 1291-1300).

Despite the advantages of IVC over in vivo enzyme selection techniques, these previously-practiced IVC methods are not suitable for enhancing enzyme activity toward insoluble substrates such as cellulosic biomass. Previous IVC methods require a soluble gene-linked substrates that is converted into a product that remains linked to the gene or an unnatural fluorogenic substrate as described above. In both cases, enzymes selected using these methods do not exhibit increased activity toward insoluble, naturally-occurring substrates.

Therefore, it was desirable to develop an enzyme enhancement system that enabled targeting of enzyme activity on a relevant insoluble solid-phase substrate and that was performed in vitro to eliminate organism metabolic and genomic background effects that are present in vivo. In general, the scheme of the invention operates in selection mode, where variants with desirable catalytic properties are selected in the background of a population of undesirable variants. In addition, the selection can be carried out on a population size of billions of variants or more in order to effectively sample the enzyme optimization landscape.

General Selection Method

The invention provides a selection method for enhanced enzyme activity on an insoluble substrate. The method employs a collection of polynucleotides encoding variants of one or more enzyme(s) that act(s) on an insoluble substrate, such as a polynucleotide library. The collection of polynucleotides is linked to a collection of solid phases, such as microbeads or particles. The linker or the solid phases include a substrate for the one or more enzyme(s), such that the activity of the enzyme type encoded in the polynucleotides can release the polynucleotides from the solid phases, either by cleaving the linker or by degrading the microbead or particle.

In particular embodiments, the method entails suspending the polynucleotide-linked solid phases in an aqueous phase comprising components for in vitro transcription/translation. The aqueous phase is used to form a water-in-oil emulsion, wherein the polynucleotide-linked solid phases are compartmentalized in aqueous droplets in an oil continuous phase. The aqueous phase of the emulsion includes the reagents necessary for in vitro transcription/translation, and the emulsion is maintained on conditions suitable for these processes, such that enzyme variants encoded in the polynucleotides are expressed within the aqueous droplets of the emulsion. An active enzyme variant in a given aqueous droplet will cleave the linker attaching the polynucleotide(s) in that droplet to the microbead or particle and/or will degrade the microbead or particle attached to the polynucleotide. In this manner, polynucleotides are released from the microbeads or particles into the aqueous phase. The emulsion is broken, and the aqueous phase is separated from the solid and oil phases to recover polynucleotides that have been released from the solid phases, thereby allowing selection of polynucleotides encoding active enzyme variants. If desired, further genetic variation can be introduced into the recovered polynucleotides, e.g., by error-prone polymerase chain reaction (PCR), and the method repeated.

Polynucleotides

Polynucleotides useful in the invention encode an enzyme or enzyme variant and can include suitable regulatory sequences, such as those required for efficient expression of the gene product, for example promoters, enhancers, translational initiation sequences, polyadenylation sequences, splice sites and the like.

In certain embodiments, the methods of the present invention are useful for sorting libraries of polynucleotides. In particular embodiments, the methods employ libraries having at least about: $10^2$, $10^3$, $10^4$, $10^5$, $10^6$, $10^7$, $10^8$, $10^9$, $10^{10}$, $10^{11}$, and $10^{12}$ different polynucleotides. Generally, the size of the library will be less than about $10^{15}$ different polynucleotides.

Libraries of polynucleotides can be created in any of a variety of different ways that are well known to those of skill in the art. In particular, pools of naturally occurring polynucleotides can be cloned from genomic DNA or cDNA (Sambrook et al., 1989); for example, phage antibody libraries, made by PCR amplification repertoires of antibody genes from immunised or unimmunised donors have proved very effective sources of functional antibody fragments (Winter et al., 1994; Hoogenboom, 1997). Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped oligonucleotide synthesis. Libraries can also be made by introducing mutations into a polynucleotide or pool of polynucleotides randomly by a variety of techniques in vivo, including; using mutator strains, of bacteria such as *E. coli* mutD5 (Liao et al., 1986; Yamagishi et al., 1990; Low et al., 1996); using the antibody hypermutation system of B-lymphocytes (Yelamos et al., 1995). Random mutations can also be introduced both in vivo and in vitro by chemical mutagens, and ionizing or UV irradiation (see Friedberg et al., 1995), or incorporation of mutagenic base analogues (Freese, 1959; Zaccolo et al., 1996). Random mutations can also be introduced into genes in vitro during polymerization for example by using error-prone polymerases (Leung et al., 1989). Further diversification can be introduced by using homologous recombination either in vivo (see Kowalczykowski et al., 1994 or in vitro (Stemmer, 1994a; Stemmer, 1994b)). Libraries of complete or partial genes can also be chemically synthesized from sequence databases or computationally predicted sequences.

Solid Phases

Polynucleotides of the invention are attached to solid phases, which can, but need not be, an insoluble substrate for the enzyme or enzyme variant encoded by the polynucleotides. Materials useful as solid phases in the invention can include: natural polymeric carbohydrates and their synthetically modified, crosslinked, or substituted derivatives, such as agar, agarose, cross-linked alginic acid, chitin, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins, and keratins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxies; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

Solid phases generally have a size and shape that permits their suspension in an aqueous medium, followed by formation of a water-in-oil emulsion. Suitable solid phases include microbeads or particles (both termed "microparticles" for ease of discussion). Microparticles useful in the invention can be selected by one skilled in the art from any suitable type of particulate material and include those composed of cellulose, Sepharose, polystyrene, polymethylacrylate, polypropylene, latex, polytetrafluoroethylene, polyacrylonitrile, polycarbonate, or similar materials. Preferred microparticles include those averaging between about 0.01 and about 35 microns, more preferably between about 1 to 20 microns in diameter, haptenated microparticles, microparticles impregnated by one or preferably at least two fluorescent dyes (particularly those that can be identified after individual isolation in a flow cell and excitation by a laser), ferrofluids (i.e., magnetic particles less than about 0.1 micron in size), magnetic microspheres (e.g., superparamagnetic particles about 3 microns in size), and other microparticles collectable or removable by sedimentation and/or filtration.

Linkage of Polynucleotides to Solid Phases

Polynucleotides are linked to the solid phases by any means known to those in the art that do not interfere with transcription/translation. In preferred embodiments, the linker is attached to an end of each polynucleotide, thereby anchoring the polynucleotide to the solid phase. If the solid phase is not a substrate for the enzymes/enzyme variants encoded by the polynucleotides, the linker is or includes a moiety that can be cleaved by the enzyme and/or active variants to release the polynucleotides from the solid phases.

In various embodiments, approximately: 1, 2, 3, 4, 5, or 6 (or any range with these values as endpoints) different polynucleotides are linked to a single solid phase. In preferred embodiments, the different polynucleotides encode different types of enzymes, e.g., enzymes that work in concert to degrade a particular type of insoluble substrate.

One way in which the polynucleotide may be linked to a solid phase is through epoxy conjugation. This can be done by activating the solid phase (i.e., cellulose microparticles 1 to 20 μm in diameter) by using a bifunctional epoxide such as 1,4-butanediol diglycidyl ether. PCR amplification of the polynucleotide with a 5'-amino-modified primer can be used to introduce a covalently linked primary amine. In other embodiments, the amino modification may be internal. An amino-modified or unmodified polynucleotide may be covalently coupled to the epoxy-activated solid phase through an epoxy ring-opening conjugation.

In illustrative embodiments, the polynucleotide may be linked to a solid phase is through a heterobifunctional cross-linker. This can be done by activating the solid phase (i.e., cellulose microparticles 1 to 20 μm in diameter) by using an oxidizing agent such as sodium metaperiodate. PCR amplification of the polynucleotide with an amino-modified primer can be used to introduce a covalently linked primary amine. Alternatively, the amino modification may be internal. An amino-modified polynucleotide may be covalently coupled to aldehyde groups generated during oxidizing the solid phase through a heterobifunctional cross-linker such as succinimidyl 4-hydrazinonicotinate acetone hydrazone.

Another way in which the polynucleotide may be linked to a solid phase is through biotinylation. This can be done by PCR amplification with a biotinylation primer (e.g., a 5'-biotinylation primer) such that the biotin and polynucleotide are covalently linked. A biotinylated polynucleotide may be coupled to a polystyrene microbead (0.035 to 10 μm in diameter) that is coated with avidin or streptavidin, that will therefore bind the biotinylated polynucleotide with very high affinity.

If the solid phase is silicon or glass, the surface must generally be activated prior to attaching polynucleotides. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the polynucleotide directly (in the cases of amino or thiol), or the activated surface can be further reacted with linkers such as glutaraldehyde, bis (succinimidyl) suberate, SPPD 9 succinimidyl 3[2-pyridyldithio]propionate), SMCC (succinimidyl-4-[Nmaleimidomethyl]cyclohexane-1-carboxylate), SIAB (succinimidyl [4iodoacetyl]aminobenzoate), and SMPB (succinimidyl 4-[1 maleimidophenyl]butyrate) to separate the polynucleotide from the surface. Vinyl groups can be oxidized to provide a means for covalent attachment. Vinyl groups can also be used as an anchor for the polymerization of various polymers such as poly-acrylic acid, which can provide multiple attachment points for specific polynucleotides. Amino groups can be reacted with oxidized dextrans of various molecular weights to provide hydrophilic linkers of different size and capacity. Additionally, polyelectrolyte interactions can be used to immobilize a specific polynucleotide on a solid phase using techniques and chemistries described U.S. applicationSer. No. 150,278, filed Jan. 29, 1988, and U.S. application Ser. No. 375,029, filed Jul. 7, 1989, each of which is incorporated herein by reference.

Formation of Aqueous Phases Containing In Vitro Transcription/Translation Reagents According to the invention, the polynucleotide-linked solid phases are suspended in an aqueous phase including components for in vitro transcription/translation. Such components can be selected for the requirements of a specific system from the following: a suitable buffer, an in vitro transcription/replication system and/or an in vitro translation system containing all the necessary ingredients, enzymes and cofactors, RNA polymerase, nucleotides, transfer RNAs, ribosomes and amino acids (natural or synthetic).

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

Exemplary in vitro translation systems can include a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

Formation of Emulsions

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an oil) as the matrix in which these droplets are suspended (the nondisperse, continuous or external phase). Such emulsions are termed water-in-oil (W/O).

The emulsion may be stabilized by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™ 80; ICI) and polyoxyethylenesorbitan monooleate (Tween™ 80; ICI).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the polynucleotides and/or the activity of the enzymes/enzyme variants. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalization.

Creation of an emulsion generally requires the application of mechanical energy to force the phases together. There are a variety of ways of doing this that utilize a variety of mechanical devices, including stirrers (such as magnetic stirbars, propeller and turbine stirrers, paddle devices and whisks), homogenizers (including rotor-stator homogenizers, high-pressure valve homogenizers and jet homogenizers), colloid mills, ultrasound and 'membrane emulsification' devices (Becher, 1957; Dickinson, 1994).

Aqueous droplets formed in water-in-oil emulsions are generally stable with little if any exchange of polynucleotides or enzymes/enzyme variants between droplets. The technology exists to create emulsions with volumes all the way up to industrial scales of thousands of liters (Becher, 1957; Sherman, 1968; Lissant, 1974; Lissant, 1984).

The preferred droplet size will vary depending upon the precise requirements of any individual selection process that is to be performed according to the present invention. In all cases, there will be an optimal balance between polynucleotide library size, the required enrichment and the required concentration of components in the individual droplets to achieve efficient expression and reactivity of the enzymes/enzyme variants.

The processes of expression preferably occur within each individual droplet provided by the present invention. Both in vitro transcription and coupled transcription/translation become less efficient at sub-nanomolar DNA concentrations. Because of the requirement for only a limited number of DNA molecules to be present in each droplet, this therefore sets a practical upper limit on the possible droplet size. The average volume of the droplets is generally between about 1 femtoliter and about 1 nanoliter, inclusive. The average diameter of the aqueous droplets typically falls within about 1 μm and about 100 μm, inclusive. In certain embodiments, the mean volume of the droplets is preferably less than $5.2 \times 10^{-16}$ m$^3$, (corresponding to a spherical droplet of diameter less than 10 μm, more preferably less than $6.5 \times 10^{-17}$ m$^3$, (5 μm), more preferably about $4.2 \times 10^{-18}$ m$^3$ (2 μm) and most preferably about $9 \times 10^{-18}$ m$^3$ (2.6 μm).

The effective polynucleotide concentration in the droplets may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qβ replicase amplification (Miele et al., 1983; Cahill et al., 1991; Chetverin and Spirin, 1995; Katanaev et al., 1995); the ligase chain reaction (LCR) (Landegren et al., 1988; Barany, 1991); self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription/translation systems are thermostable (for example, the coupled transcription/translation systems could be made from a thermostable organism such as *Thermus aquaticus*).

Increasing the effective local nucleic acid concentration enables larger droplets to be used effectively. This allows a preferred practical upper limit for most applications to the droplet volume of about $2.2 \times 10^{-14}$ m$^3$ (corresponding to a sphere of diameter 35 μm).

The droplet size must be sufficiently large to accommodate all of the required components of the biochemical reactions that are needed to occur within the droplet, in addition to the polynucleotide-linked solid phase. In vitro, both transcription reactions and coupled transcription/translation reactions typically employ a total nucleotide concentration of about 2 mM. For example, in order to transcribe a gene to a single short RNA molecule of 500 bases in length, this would require a minimum of 500 molecules of nucleotides per droplet ($8.33 \times 10^{-22}$ moles). In order to constitute a 2 mM solution, this number of molecules must be contained within a droplet of volume $4.17 \times 10^{-19}$ liters ($4.17 \times 10^{-22}$ m$^3$ which if spherical would have a diameter of 93 nm.

Furthermore, the ribosomes necessary for the translation to occur are themselves approximately 20 nm in diameter. Hence, the preferred lower limit for droplets is a diameter of approximately 0.1 μm (100 nm).

The size of emulsion droplets may be varied simply by tailoring the emulsion conditions used to form the emulsion according to requirements of the selection system. The larger the droplet size, the larger is the volume that will be required to emulsify a given polynucleotide library, since the ultimately limiting factor will be the size of the droplet and thus the number of droplets possible per unit volume. In exemplary embodiments, the emulsion includes at least about: $10^2$, $10^3$, $10^4$, $10^5$, $10^6$, $10^7$, $10^8$, $10^9$, $10^{10}$, $10^{11}$, and $10^{12}$ droplets/mL of emulsion.

Depending on the complexity and size of the library to be screened, it may be beneficial to form an emulsion such that in general 1 or less than 1 polynucleotide-linked solid phase is included in each droplet of the emulsion. The number of polynucleotides per droplet is governed by the Poisson distribution. Accordingly, if conditions are adjusted so that there are, on average, 0.1 polynucleotide-linked solid phase per droplet, then, in practice, approximately: 90% of droplets will contain no polynucleotide-linked solid phase, 9% of droplets will contain 1 polynucleotide-linked solid phase, and 1% of droplets will contain 2 or more polynucleotide-linked solid phases. In practice, average values of about 0.1 to about 0.5, more preferably about 0.3, polynucleotide-linked solid phases per droplet provide emulsions that contain a sufficiently high percentage of droplets having 1 polynucleotide-linked solid phase per droplet, with a sufficiently low percentage of droplets having 2 or more polynucleotide-linked solid phases per droplet. This approach will generally provide the greatest power of resolution. Where the library is larger and/or more complex, however, this may be impracticable; it may be preferable to include several polynucleotide-linked solid phases together and rely on repeated application of the method of the invention to achieve sorting of the desired activity. In various embodiments, the water-in-oil emulsion is formed under conditions wherein at least about: 20%, 30%, 40%, 50%, 60%, 70%, 80%, or 90% of aqueous droplets include 1 or less than 1 polynucleotide-linked solid phase.

Theoretical studies indicate that the larger the number of polynucleotide variants created the more likely it is that a molecule will be created with the properties desired (see Perelson and Oster, 1979 for a description of how this applies to repertoires of antibodies). Recently it has also been confirmed practically that larger phage-antibody repertoires do indeed give rise to more antibodies with better binding affinities than smaller repertoires (Griffiths et al., 1994). To ensure that rare variants are generated and thus are capable of being selected, a large library size is generally desirable.

Using the present invention, at a preferred aqueous droplet diameter of 2.6 µm, a repertoire size of at least $10^{11}$ can readily be sorted using 1 ml aqueous phase in a 20 ml emulsion.

Recovery of Released Polynucleotides

The emulsion is maintained for a sufficient time under conditions suitable for transcription/translation of the enzymes/enzyme variants. The enzymes/enzyme variants act to cleave a cleavable linker attaching the polynucleotides to the solid phases, if present, and/or to degrade solid phases that consist of an insoluble substrate for the enzyme. Enzyme activity thus results in the release of polynucleotides encoding active enzymes/enzyme variants from their solid phases into the aqueous phase.

The aqueous phase is separated from the solid and oil phases by any suitable technique, such as, for example sedimentation using a centrifuge. The released polynucleotides can then be recovered from the aqueous phase by any of a number of conventional techniques.

After each round of selection, the enrichment of the pool of polynucleotides for those encoding the molecules of interest can be assayed by non-compartmentalised transcription/translation reactions. The selected pool can be amplified and/or cloned into a suitable vector for propagation and/or expression. RNA and/or recombinant protein can produced from the individual clones for further purification and assay. Recombinant enzyme variants selected using the methods of the invention can be employed for any application for which the native enzyme is employed. Thus, for example, a cellulase variant can be contacted with a cellulosic substrate, e.g., biomass. In an exemplary embodiment, the biomass is in the form of particulate matter, wherein the average particle diameter is in the range of 1 to 100 µm. In this matter, a cellulose variant of the invention can be employed in the production of a biofuel.

Exemplary Embodiments

The system and method of the present invention will be described in connection with enzymes expressed from synthetic DNA gene sequences. However, the system and method may also be used with DNA sequences derived from natural sources or with synthetic or natural RNA gene sequences.

Figure 2:
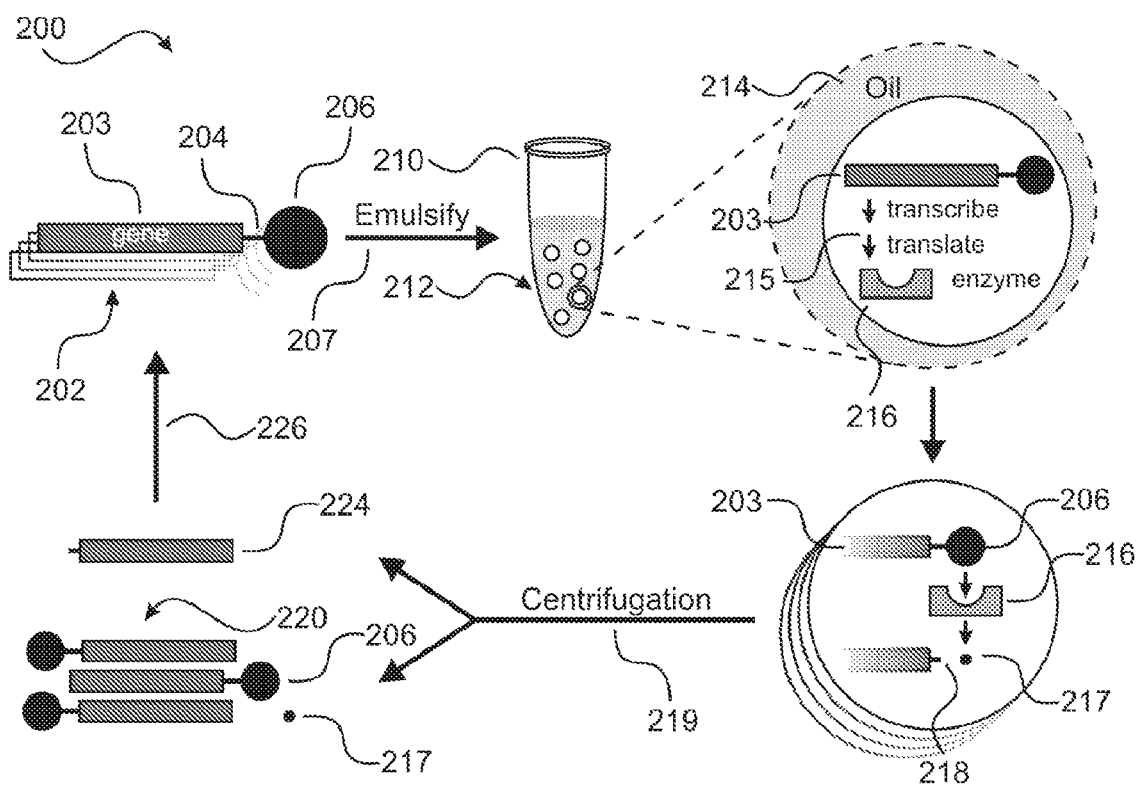
FIG. 2 is a diagrammatic representation of the process steps involved in enzyme selection in accordance with the present invention.

As shown by FIG. 2, the enzyme selection process 200, in one embodiment, begins with the creation of a polynucleotide library (202). More specifically, the polynucleotide library may be created from a gene sequence encoding an enzyme with activity toward the targeted insoluble substrate. Examples of insoluble substrates and the enzymes that catalyzed their degradation are shown in the table below.

| Class | Examples | Enzymes |
| --- | --- | --- |
| Insoluble polysaccharides | Cellulose, hemicellulose, chitin, sepharose | Cellulase, hemicellulase, chitinase, agarase |
| Insoluble proteins | Amyloids, keratins | Neprilysin, protease, keratinase |
| Organic polymers, plastics | Lignin, polylactic acid, polybutylene succinate, polycaprolactone, polyhydroxybutyrate | Lignin peroxidase, lipase, cutinase |

For example, Sequence 1, encoding the endoglucanase gene egl1 from *Trichoderma reesei*, may be used for substrates or linkers composed of cellulose. Similarly, Sequence 2, encoding the ligninase gene LiP H8 from *Phanerochaete chrysosporium*, may be used for substrates or linkers composed of lignin. The sequences may be chemically synthesized by various vendors (e.g. Biomatik Corp., BioPioneer, Codon Devices, Exon BioSystems, and Molecular Cloning Laboratories). The gene sequences may include a transcription initiation site such as the T7 promoter sequence as well as the Kozak ribosomal binding signal sequence for efficient transcription and translation in the in vitro transcription/translation (IVTT) reaction described below. The sequence 5'-(N)$_{10}$-TAATACGACTCACTATAGGGAGAGCCACCATGG-3' can be added to the gene sequence to provide these transcription initiation and ribosomal binding sites.

Gene variants (203) within the polynucleotide library (202) may be created by using mutagenic amplification. More specifically, 10 µL of 10× mutagenic PCR buffer (70 mM MgCl$_2$, 500 mM KCl, 100 mM Tris-HCl pH 8.3, 0.1% (w/v) gelatin) is combined with 10 µL of 10× dNTP mix (2 mM dGTP, 2 mM dATP, 10 mM dCTP, 10 mM dTTP), 30 pmol of 5'-amino-modified forward PCR primer, 30 pmol or reverse PCR primer, 20 fmol of gene Sequence 1 or 2, and brought to a total volume to 88 µL with water. Next, 10 µL of 5 mM MnCl$_2$ and 5 units (2 µL) of Taq DNA polymerase are added for a final volume to 100 µL. The solution is mixed gently by pipetting. The reaction is thermal cycled 30× for 1 minute at 94° C., 1 minute at 45° C., and 1 minute at 72° C.

Mutagenic amplification using a 5'-amino-modified forward PCR primer provides one means of linking (204) gene variants (203) to an insoluble microparticle (206). The microparticles may be cellulose microparticles (SigmaCell S3504, Sigma-Aldrich) prepared as follows: 1 g of microparticles is washed with 100 ml of 95% ethanol, 100 ml of water, and 20 ml of 0.6 N NaOH. The microparticles are combined with 2.5 ml of 1,4-butanediol diglycidyl ether (Eastman Kodak) and 2.5 ml of 0.6 N NaOH containing 4 mg/ml NaBH$_4$. The reaction is carried out at room temperature for 18 h with continuous stirring. The reaction is stopped by washing with water until neutral pH is achieved. Washing with 50-mL of 95% ethanol removes residual 1,4-butanediol diglycidyl ether. 5'-amino-modified gene variants (203) are linked (204) to the prepared microparticles (206) in 0.1 N NaOH at 21° C. for 4-8 h in a stoichiometric ratio of 1:3 to 1:10 such that in general only one gene variant (203) is linked (204) to any given microbead (206) as dictated by the Poisson distribution. See, (Moss, L. G., et al., "A simple, efficient method for coupling DNA to cellulose." *J. Bio. Chem.*, 1981, 256(24): 12655-12658).

In an alternative, illustrative embodiment, mutagenic amplification using an amino-modified PCR is used to link (204) gene variants (203) to an insoluble microparticle (206), such as a cellulose microparticle (SigmaCell S3504, Sigma-Aldrich), is carried out as follows: 5 mg of microparticles is washed with 3×40 ml of water, and 3×40 ml of 100 mM sodium acetate. The microparticles are oxidized in a 100 mM sodium metaperiodate, 100 mM sodium acetate solution for 1 hr at room temperature. The solution is then removed by washing the microparticles 3×40 ml of water. Amino-modified gene variants are activated with a heterobifunctional cross-linker by combining 10% w/v succinimidyl 4-hydrazinonicotinate acetone hydrazone dissolved in dimethylformamide with 5 µg gene variants in 1× phosphate buffered saline for 3 h at room temperature. Activated gene variants are purified from residual heterobifunctional cross-linker and exchanged into 1×2-(N-morpholino)ethanesulfonic acid saline buffer by using a NAP-5 column (GE Healthcare Life Sciences). Activated gene variants (203) are linked (204) to the prepared microparticles (206) in 1×2-(N-morpholino) ethanesulfonic acid saline buffer at 21° C. for 1 h in a stoichiometric ratio of 1:3 to 1:10 such that in general only one gene variant (203) is linked (204) to any given microbead (206) as dictated by the Poisson distribution. See, (Bioconjugate Techniques, 2nd Edition, Greg T. Hermanson, Published by Academic Press, Inc., 2008).

The polynucleotide library (202) may be emulsified (207) using the following procedure: Oil-surfactant mixture (214) (4% v/v polysiloxane-polycetyl-polyethylene glycol copolymer (Abil EM90, Goldschmidt) dissolved in light mineral oil) is prepared and 950 µL is transferred to a CryoTube vial (1.8 ml, round bottoms, star-feet; Nunc), cooled on ice, and a magnetic stir bar is added. The mixture is stirred at 1,150 r.p.m on a magnetic stirrer. The IVTT reaction mixture is prepared (35 µL EcoPro T7 (Promega), 2 µL 5 mM methionine, 1.66 fmol polynucleotide library (202), water up to 50 µL) and added to the oil-surfactant mixture (214) in 10-1 µL aliquots over a 2 min period to generate emulsion (210) containing $10^{10}$–$10^{12}$ droplets (212) (compartments). The emulsion is incubated at 23-30° C. for 1-4 h to allow for transcription and translation (215) of gene variant (203) into protein enzyme variant (216).

Once translated, enzyme variant (216) begins to degrade the cellulose microparticle (206). Gene variants (203) encoding enzyme variants (216) that exhibit enhanced activity toward the cellulose microparticle (206) degrade the microparticle (217). Such gene variants are probabilistically more likely to be released (218) from the degraded microparticle (217) than gene variants encoding enzyme variants exhibiting lower activity. A variable incubation period of 1-4 h tunes the assay stringency. In practice, one starts with a longer incubation time and progressively shortens the incubation time through subsequent rounds of selection as the enzyme is refined to a more active state. After incubation, the emulsion (210) is broken by centrifugation (219) at 13,000 g for 5 min at 25° C. Gene variants (220) encoding enzymes with low or no activity toward the microparticle (206) co-precipitate with the microparticles (206) during centrifugation (219). Degraded microparticles (217) also precipitate during centrifugation (219). Gene variants (224) encoding enzyme variants exhibiting enhanced activity remain suspended in aqueous solution and are thus selectively enriched via negative selection of microparticle-bound gene variants (206,202). Gene variants (224) may be recovered from the aqueous solution by using PCR, e.g., the QIAquick PCR Purification Kit (Qiagen), and subjected to additional rounds (226) of mutagenic amplification and selection to further enhance enzyme activity.

Process 200 is distinct from that presented in FIG. 1 (100) in which the substrate (106), product (118), and gene variant (103) remained linked (104) and in which positive selection is performed by means of affinity capture (122, 123) of the product (118).

While the invention has been particularly shown and described with reference to specific embodiments, it will also be understood by those skilled in the art that changes in the form and details of the disclosed embodiments may be made without departing from the spirit or scope of the invention. For example, the embodiments described above may be implemented using a variety of insoluble substrates, linkers, microparticles, and gene sequences. Furthermore, techniques and mechanisms of the present invention have sometimes been described in singular form for clarity. However, it should be noted that some embodiments can include multiple iterations of a technique or multiple applications of a mechanism unless noted otherwise. Therefore, the scope of the invention should be determined with reference to the appended claims.

What is claimed is:

1. A selection method for enhanced enzyme activity on an insoluble substrate, the method comprising:
   (a) providing a plurality of polynucleotides encoding variants of one or more enzyme(s) that act(s) on an insoluble substrate, wherein the plurality of polynucleotides is linked to a plurality of solid phases and the linker or the solid phases comprise a substrate for the one or more enzyme(s);
   (b) suspending the polynucleotide-linked solid phases in an aqueous phase comprising components for in vitro transcription/translation;
   (c) forming a water-in-oil emulsion, wherein the polynucleotide-linked solid phases are compartmentalized in aqueous droplets in an oil continuous phase;
   (d) carrying out in vitro transcription/translation to express enzyme variants within aqueous droplets of the emulsion, wherein an active enzyme variant in an aqueous droplet releases the polynucleotide(s) from the solid phase-in that droplet; and
   (e) separating the aqueous phase from the solid and oil phases to recover
   polynucleotides in the aqueous phase that have been released from the solid phases.

2. The method of claim 1, wherein the plurality of polynucleotides comprises at least $10^6$ different polynucleotides.

3. The method of claim 1, wherein each polynucleotide-linked solid phase comprises 1-6 different polynucleotides, each of which is present in one or more copies.

4. The method of claim 3, wherein said 1-6 different polynucleotides encode 1-6 different types of enzymes.

5. The method of claim 1, wherein the solid phases comprise microbeads or particles.

6. The method of claim 1, wherein the water-in-oil emulsion is formed under conditions wherein at least about 20% of aqueous droplets comprise 1 or less than 1 polynucleotide-linked solid phase.

7. The method of claim 6, wherein each polynucleotide-linked solid phase comprises 1 to 6 polynucleotides, each of which is present in one or more copies, whereby, 1 to 6, respectively, enzyme variants are expressed per aqueous droplet containing a polynucleotide-linked solid phase.

8. The method of claim 1, wherein the emulsion comprises at least about $10^9$ aqueous droplets/mL of emulsion.

9. The method of claim 1, wherein the aqueous phase is separated from the solid and oil phases by sedimentation using a centrifuge.

10. The method of claim 1, wherein recovered polynucleotides are amplified and linked to a plurality of solid phases, wherein the linker or the solid phases comprise a substrate for the one or more enzyme(s), and steps (b)-(e) are repeated.

11. The method of claim 1, wherein recovered polynucleotides are mutagenized and then linked to a plurality of solid phases, wherein the linker or the solid phases comprise a substrate for the one or more enzyme(s), and steps (b)-(e) are repeated.

12. The method of claim 1, wherein the one or more of the recovered polynucleotides are translated in vitro to produce one or more enzyme variants.

13. The method of claim 1, wherein one or more of the recovered polynucleotides are cloned into a vector.

14. The method of claim 13, wherein the vector comprises an expression vector, and the method additionally comprises:
   (a) expressing one or more of the recovered polynucleotides to produce one or more enzyme variants;
   (b) recovering the one or more enzyme variants from the culture; and
   (c) contacting the one or more enzyme variants with an insoluble substrate.

15. The method of claim 14, wherein the insoluble substrate comprises biomass.

16. The method of claim 1, wherein the linker comprises a substrate for the one or more enzyme(s).

17. The method of claim 1, wherein the solid phases comprise a substrate for the one or more enzyme(s).

* * * * *

SEQUENCE LISTING

```
<160> NUMBER OF SEQ ID NOS: 2

<210> SEQ ID NO 1
<211> LENGTH: 1500
<212> TYPE: DNA
<213> ORGANISM: Trichoderma reesei

<400> SEQUENCE: 1
ttgtcccaaa atggcgccct cagttacact gccgttgacc acggccatcc tggccattgc      60
ccggctcgtc gccgcccagc aaccgggtac cagcaccccc gaggtccatc ccaagttgac     120
aacctacaag tgtacaaagt ccgggggggtg cgtggcccag gacacctcgg tggtccttga     180
ctggaactac cgctggatgc acgacgcaaa ctacaactcg tgcaccgtca acggcggcgt     240
caacaccacg ctctgccctg acgaggcgac ctgtggcaag aactgcttca tcgagggcgt     300
cgactacgcc gcctcgggcg tcacgacctc gggcagcagc ctcaccatga accagtacat     360
gcccagcagc tctggcggct acagcagcgt ctctcctcgg ctgtatctcc tggactctga     420
cggtgagtac gtgatgctga agctcaacgg ccaggagctg agcttcgacg tcgacctctc     480
tgctctgccg tgtggagaga acggctcgct ctacctgtct cagatggacg agaacgggg      540
```

```
cgccaaccag tataacacgg ccggtgccaa ctacgggagc ggctactgcg atgctcagtg      600
ccccgtccag acatggagga acggcaccct caacactagc caccagggct tctgctgcaa      660
cgagatggat atcctggagg gcaactcgag ggcgaatgcc ttgacccctc actcttgcac      720
ggccacggcc tgcgactctg ccggttgcgg cttcaacccc tatggcagcg gctacaaaag      780
gtgagcctga tgccactact accccttttcc tggcgctctc gcggttttcc atgctgacat      840
ggttttccag ctactacggc cccggagata ccgttgacac ctccaagacc ttcaccatca      900
tcacccagtt caacacggac aacggctcgc cctcgggcaa ccttgtgagc atcacccgca      960
agtaccagca aaacggcgtc gacatcccca gcgcccagcc cggcggcgac accatctcgt     1020
cctgcccgtc cgcctcagcc tacggcggcc tcgccaccat gggcaaggcc ctgagcagcg     1080
gcatggtgct cgtgttcagc atttggaacg acaacagcca gtacatgaac tggctcgaca     1140
gcggcaacgc cggcccctgc agcagcaccg agggcaaccc atccaacatc ctggccaaca     1200
accccaacac gcacgtcgtc ttctccaaca tccgctgggg agacattggg tctactacga     1260
actcgactgc gccccgccc cgcctgcgt ccagcacgac gttttcgact acacggagga     1320
gctcgacgac ttcgagcagc ccgagctgca cgcagactca ctgggggcag tgcggtggca     1380
ttgggtacag cgggtgcaag acgtgcacgt cgggcactac gtgccagtat agcaacgact     1440
gttcgtatcc ccatgcctga cgggagtgat tttgagatgc taaccgctaa aatacagact     1500
```

<210> SEQ ID NO 2
<211> LENGTH: 1320
<212> TYPE: DNA
<213> ORGANISM: Phanerochaete chrysosporium

<400> SEQUENCE: 2

```
ttttttcttc agtcccactc agcaccagca acacagcgga catggccttc aagcagctct       60
tcgcagctat ctctctcgct ctcttgctct cggctgcgaa cgcggctgcg gtgatcgaga      120
agcgcgccac ctgttccaac ggcaagaccg tcggcgatgc gtcgtcgtgc gcttggttcg      180
acgtcctgga tgatatccag cagaacctgt ccacggcgg ccagtgcggc gctgaggcgc      240
acgagtcgat tcgtctcgtc ttccacgact ccatcgcaat ttcgcccgcc atggaggcac      300
agggcaagtt cggcggcggt ggtgctgacg gctccatcat gatcttcgac gatatcgaga      360
ctgcgttcca ccctaacatc ggtctcgacg agatcgtcaa gctccagaag ccattcgttc      420
agaagcacgg tgtcaccccct ggtgacttca tcgccttcgc tggtcgtgtc gcgctcagca      480
actgccctgt tgccccgcag atgaacttct tcactggtcg tgcacctgct acccagcccg      540
ctcctgatgg ccttgtcccc gagcccttcc acactgtcga ccaaatcatc aaccgtgtca      600
acgacgcagg cgagttcgat gagctcgagc ttgtctggat gctctccgcg cactccgtcg      660
cagcggtgaa cgacgtcgac ccgaccgtcc agggtctgcc ctttgactcg accccggaa      720 tcttcgactc ccagttcttc gtcgagactc agcttcgtgg taccgccttc cccggctctg      780
gtggcaacca aggcgaggtc gagtcgccgc tccctggcga attcgcatc cagtccgacc      840 acactatcgc ccgcgactcg cgcacggcgt gtgaatggca gtccttcgtc aacaaccagt      900
ccaagctcgt cgatgacttc cagttcatct tcctcgccct cacccagctc ggccaggacc      960
cgaacgcgat gaccgactgc tcggatgtta tcccgcagtc caagcccatc cctggcaacc     1020
tcccattctc gttcttcccc gctggcaaga ccatcaagga cgttgagcag gcgtgtgcgg     1080
agagcccctt ccgactctca ccactctccc ggggcccgag acgtccgtcc agcgcatccc     1140
tccgcctccg ggtgcttaaa tgatgccata cagaatactc ctcaaaccga ctgtaacggt     1200
```

-continued

```
ggccggctaa ctcgtgacgg aacttcggct ttactagatt tcattcatcg tatctctgca    1260
cctaactacg aatctcattc gtctacttcc ttcttacgat attccttgcg cgtgggctta    1320
```